(12) United States Patent
Schwint et al.

(10) Patent No.: US 10,017,431 B2
(45) Date of Patent: Jul. 10, 2018

(54) PROCESS FOR CO-PRODUCING C3 OLEFINS, IC4 OLEFINS, NC4 OLEFINS AND DIOLEFINS, AND/OR C5 OLEFINS AND DIOLEFINS

(71) Applicant: Lummus Technology Inc., Bloomfield, NJ (US)

(72) Inventors: Kevin John Schwint, Long Valley, NJ (US); Robert John Brummer, Wharton, NJ (US)

(73) Assignee: Lummus Technology Inc., Bloomfield, NJ (US)

( * ) Notice: Subject to any disclaimer, the term of this patent is extended or adjusted under 35 U.S.C. 154(b) by 0 days.

(21) Appl. No.: 14/565,913

(22) Filed: Dec. 10, 2014

(65) Prior Publication Data

US 2016/0168052 A1    Jun. 16, 2016

(51) Int. Cl.
  *C07C 5/333*    (2006.01)
  *C07C 41/01*    (2006.01)
  *B01J 8/02*    (2006.01)

(52) U.S. Cl.
  CPC .......... *C07C 5/333* (2013.01); *B01J 8/02* (2013.01); *B01J 2208/00008* (2013.01); *B01J 2208/021* (2013.01)

(58) Field of Classification Search
  CPC .. C07C 5/333; C07C 41/01; B01J 8/02; B01J 2208/00008; B01J 2208/021
  See application file for complete search history.

(56) References Cited

U.S. PATENT DOCUMENTS

| 2,831,041 | A | * | 4/1958 | Sieg | C07C 5/321 |
| | | | | | 208/136 |
| 3,092,674 | A | * | 6/1963 | Bray, Jr. | C07C 5/333 |
| | | | | | 422/218 |
| 4,581,339 | A | * | 4/1986 | Bhatt | C07C 5/3332 |
| | | | | | 502/38 |
| 5,105,024 | A | * | 4/1992 | McKay | C07C 5/3337 |
| | | | | | 568/697 |

(Continued)

OTHER PUBLICATIONS

International Search Report and Written Opinion dated Feb. 1, 2016 in corresponding International application No. PCT/US2015/057480 (10 pages).

(Continued)

*Primary Examiner* — Brian A McCaig
*Assistant Examiner* — Jason Y Chong
(74) *Attorney, Agent, or Firm* — Osha Liang LLP (57) ABSTRACT

Processes and systems for producing olefins, including: dehydrogenating a first n-alkane to produce a first effluent; and dehydrogenating at least one of a first isoalkane or a second n-alkane to produce a second effluent. The first and second effluents may be compressed and fed to a common separation train to separate the effluents into two or more fractions. In some embodiments, each of the first and second dehydrogenation reaction zones may include two reactors, one reactor in each of the reaction zones operating in a dehydrogenation cycle, one operating in a regeneration cycle, and one operating in a purge or evacuation/reduction cycle. Operation of the reactors in the dehydrogenation cycle is staggered, such that the purge cycle, regeneration cycle, or evacuation/reduction cycle of the reactors may not overlap.

21 Claims, 7 Drawing Sheets

(56) References Cited

U.S. PATENT DOCUMENTS

| | | | | |
|---|---|---|---|---|
| 5,214,225 A | * | 5/1993 | Hall | C07C 5/333 |
| | | | | 585/654 |
| 5,220,093 A | * | 6/1993 | Gartside | C07C 5/333 |
| | | | | 585/654 |
| 5,527,979 A | | 6/1996 | Agaskar et al. | |
| 5,563,314 A | | 10/1996 | Agaskar et al. | |
| 5,750,798 A | | 5/1998 | Scharre et al. | |

OTHER PUBLICATIONS

Office Action issued in corresponding Chinese Application No. 201510895549.6 dated Sep. 4, 2017, and English translation thereof (19 pages).

\* cited by examiner

PROCESS FOR CO-PRODUCING C3 OLEFINS, IC4 OLEFINS, NC4 OLEFINS AND DIOLEFINS, AND/OR C5 OLEFINS AND DIOLEFINS

FIELD OF THE DISCLOSURE

Embodiments disclosed herein relate generally to an improved process for the production of olefins and diolefins, including propylene, isobutene, normal butenes and butadiene, and in some embodiments isopentene and isoprene.

BACKGROUND

Olefin and diolefin hydrocarbons are useful for the production of a number of petrochemical products, such as polymers, motor fuel blending additives, and other products. Short chain saturated hydrocarbons having from 2 to 5 carbon atoms per molecule are often subjected to dehydrogenation to form the corresponding olefin. The olefins, in turn, may be used in the alkylation of isoparaffins, in the etherification of alcohols to make motor fuel blending additives, or as monomers used to produce various polymer materials. Olefins can also undergo subsequent dehydrogenation to diolefins.

One particularly useful olefin is propylene, which may be produced by dehydrogenation of propane. Propylene is the world's second largest petrochemical commodity and is used in the production of polypropylene, acrylonitrile, acrylic acid, acrolein, propylene oxide and glycols, plasticizer oxo-alcohols, cumene, isopropyl alcohol and acetone. The growth in propylene production is primarily driven by the industry demand for polypropylene, which is used in such everyday products as packaging materials and outdoor clothing. Other useful olefins include normal butenes, isobutene, and isopentene, which have equally diverse end uses.

One particularly useful diolefin is butadiene, which may be produced by dehydrogenation of n-butene. Butadiene is used primarily as a chemical intermediate and as a monomer in the manufacture of polymers such as synthetic rubbers or elastomers, including styrene-butadiene rubber (SBR), polybutadiene rubber (PBR), polychloroprene (Neoprene) and nitrile rubber (NR). Another useful diolefin is isoprene. The major applications of isoprene include use as a monomer for the manufacture of polyisoprene rubber, styrene-isoprene-styrene block copolymers (SIS) and butyl rubber.

The desired olefin and diolefin products, such as propylene, isobutene, normal butenes, butadiene, isopentene and isoprene are generally produced in separate, non-integrated, systems, one system producing propylene from propane, one system for producing isobutene from isobutane, a third system for producing normal butenes and/or butadiene from n-butane (or butadiene from n-butenes), and a fourth system for producing isopentene and/or isoprene from isopentane. While it has been proposed to co-process propane, isobutane, and n-butane feeds simultaneously in a single reactor, reactor performance generally declines when the feeds are combined and processed together. This is because reaction conditions (temperature, pressure, space velocity, etc.) can only be selected to optimize the relationship among selectivity, conversion, and energy consumption for one of the products and, therefore, the other product or products are produced at non-optimal conditions.

SUMMARY OF THE CLAIMED EMBODIMENTS

Embodiments disclosed herein provide for integrated co-production of C3, C4, and C5 olefins and diolefins. As will be described further below, the integrated processes and systems herein may provide for the reaction efficiency of separate processing trains while reducing piece count as compared to such non-integrated systems.

In one aspect, embodiments disclosed herein relate to a process for producing olefins. The process may include dehydrogenating a first n-alkane in a first dehydrogenation reaction zone to produce a first effluent comprising at least one of a first n-olefin or a first diolefin. The process may also include dehydrogenating at least one of a first isoalkane or a second n-alkane in a second dehydrogenation reaction zone to produce a second effluent comprising at least one of a first isoolefin, a second n-olefin, or a second diolefin. The first and second effluents may be compressed and fed to a common separation train to separate the first olefin, the first isoolefin or first diolefin, unreacted first n-alkane, first isoalkane or second n-alkane, and light byproducts or heavy byproducts into two or more fractions.

In some embodiments, the first n-alkane is propane, the at least one of a first n-olefin or a first diolefin is propylene, the at least one of a first isoalkane or a second n-alkane is isobutane, and the at least one of a first isoolefin, a second n-olefin, or a second diolefin is isobutene. In other embodiments, the first n-alkane is propane, the at least one of a first n-olefin or a first diolefin is propylene, the at least one of a first isoalkane or a second n-alkane is n-butane, and the at least one of a first isoolefin, a second n-olefin, or a second diolefin is at least one of n-butene and butadiene. In yet other embodiments, the first n-alkane is n-butane, the at least one of a first olefin or a first diolefin is at least one of n-butene or butadiene, the at least one of a first isoalkane or a second n-alkane is isobutane, and the first isoolefin is isobutene. In yet other embodiments, the at least one of a first isoalkane or a second n-alkane is n-butane and isobutane, the at least one of a first isoolefin, a second n-olefin or a second diolefin is at least one of isobutene, n-butene or butadiene, the first n-alkane is propane, and the at least one of a first n-olefin or a first diolefin is propylene.

The process may also include dehydrogenating at least one of a second isoalkane or a third n-alkane in a third dehydrogenation reaction zone to produce a third effluent comprising at least one of a second isoolefin, a third n-olefin, or a third diolefin. The third effluent may be compressed and fed to the common separation train. In some embodiments, the first n-alkane is propane, the at least one of a first n-olefin or a first diolefin is propylene, the at least one of a first isoalkane or a second n-alkane is at least one of n-butane and isobutane, and the at least one of a first isoolefin, a second n-olefin, or a second diolefin is at least one of n-butene, isobutene, or butadiene; and the at least one of a second isoalkane or a third n-alkane is isopentane, and the at least one of a second isoolefin, a third n-olefin, or a third diolefin is at least one of isopentene or isoprene. In other embodiments, the first n-alkane is propane, the at least one of a first n-olefin or a first diolefin is propylene, the at least one of a first isoalkane or a second n-alkane is isobutane, and the at least one of a first isoolefin, a second n-olefin, or a second diolefin is isobutene; and the at least one of a second isoalkane or a third n-alkane is n-butane, and the at least one of a second isoolefin, a third n-olefin, or a third diolefin is at least one of n-butene or butadiene.

The process may also include dehydrogenating a third isoalkane in a fourth dehydrogenation reaction zone to produce a fourth effluent comprising at least one of a third isoolefin or a fourth diolefin; compressing the fourth effluent; and feeding the fourth effluent to the common separation train. In some embodiments, the first n-alkane is propane, the at least one of a first n-olefin or a first diolefin is propylene, the at least one of a first isoalkane or a second n-alkane is n-butane, and the at least one of a first isoolefin, a second n-olefin, or a second diolefin is at least one of n-butene or butadiene; the at least one of a second isoalkane or a third n-alkane is isobutane, and the at least one of a second isoolefin, a third n-olefin, or a third diolefin is isobutene; and the third isoalkane is isopentane, and the at least one of a third isoolefin or a fourth diolefin is at least one of isopentene or isoprene.

In some embodiments, such as where each of the first and second dehydrogenation reaction zones comprise two reactors, the process may include operating one reactor in each of the reaction zones in a dehydrogenation cycle; operating one reactor in a regeneration cycle; and operating one reactor in a purge or evacuation/reduction cycle. In some embodiments, an effluent comprising steam and hydrocarbons from the reactor in a purge cycle may be combined with the second effluent. The steam may be separated from the hydrocarbons in the purge effluent and the second effluent, such as by condensing the steam in a compressor inter-stage cooler. In some embodiments, the process may also include sequentially operating two or more valves disposed in a parallel flow arrangement for providing air, steam, and inerts, as required, from a common regeneration system to the reactors in the reheat/regeneration cycle and the reactor in the purge/evacuation/reduction cycle, and for providing propane, n-butane, isobutane, or isopentane, as required, to the reactors in the dehydrogenation cycle. Operation of the reactors in the dehydrogenation cycle may also be staggered, such that the purge cycle, regeneration cycle, or evacuation/reduction cycle of the reactors do not overlap.

In some embodiments, such as where each of the first and second dehydrogenation reaction zones comprise four reactors, the process may include operating two reactors in each of the reaction zones in a dehydrogenation cycle; operating one reactor in each of the reaction zones in a regeneration cycle; and operating one reactor in each of the reaction zones in a purge or evacuation/reduction cycle. In some embodiments, operation of the reactors in the dehydrogenation cycle is staggered, such that the purge cycle, regeneration cycle, or evacuation/reduction cycle of the reactors in each of the reaction zones do not overlap.

In some embodiments, such as where each of the first and second dehydrogenation reaction zones comprise five reactors, the process may include operating two reactors in each of the reaction zones in a dehydrogenation cycle; operating two reactors in each of the reaction zones in a regeneration cycle; and operating one reactor in each of the reaction zones in a purge or evacuation/reduction cycle. In some embodiments, operation of the reactors in the dehydrogenation and regeneration cycles is staggered, such that the purge cycle or evacuation/reduction cycle of the reactors in each of the reaction zones do not overlap.

In another aspect, embodiments disclosed herein relate to a system for producing olefins. The system may include a first dehydrogenation reaction zone for dehydrogenating a first n-alkane to produce a first effluent comprising at least one of a first n-olefin or a first diolefin and a second dehydrogenation reaction zone for dehydrogenating at least one of a first isoalkane or a second n-alkane to produce a second effluent comprising at least one of a first isoolefin, a second n-olefin, or a second diolefin. The system may also include one or more compressors for compressing the first effluent and the second effluent; and a common separation train for separating the first effluent and second effluent into two or more fractions.

In some embodiments, the system may also include a third dehydrogenation reaction zone for dehydrogenating at least one of a second isoalkane or a third n-alkane to produce a third effluent comprising at least one of a second isoolefin, a third n-olefin, or a third diolefin. A flow conduit may be provided for feeding the third effluent to the common separation train.

In some embodiments, the system may also include a fourth dehydrogenation reaction zone for dehydrogenating a third isoalkane to produce a fourth effluent comprising at least one of a third isoolefin or a fourth diolefin. A flow conduit may be provided for feeding the third effluent to the common separation train.

In some embodiments, such as where each of the first and second dehydrogenation reaction zones comprise two reactors, the system may also include a control system configured for: operating one reactor in each of the reaction zones in a dehydrogenation cycle; operating one reactor in a regeneration cycle; and operating one reactor in a purge or evacuation/reduction cycle.

The system may also include, in some embodiments, a mixing device for combining an effluent comprising steam and hydrocarbons from the reactor in a purge cycle with the second effluent, and a separation system for separating the steam from the hydrocarbons in the purge effluent and the second effluent. The separation system may include a compressor inter-stage cooler, for example.

In some embodiments, the control system may be further configured for sequentially operating two or more valves disposed in a parallel flow arrangement for providing air, steam, and inerts, as required, from a common regeneration system to the reactors in the reheat/regeneration cycle and the reactor in the purge/evacuation/reduction cycle, and for providing propane, n-butane, and isobutane, as required, to the reactors in the dehydrogenation cycle. The control system may also be configured to operate the reactors in the dehydrogenation cycle in staggered cycles, such that the purge cycle, regeneration cycle, or evacuation/reduction cycle of the reactors do not overlap.

In some embodiments, such as where each of the first and second dehydrogenation reaction zones comprise four reactors, the system may include a control system configured for: operating two reactors in each of the reaction zones in a dehydrogenation cycle; operating one reactor in each of the reaction zones in a regeneration cycle; and operating one reactor in each of the reaction zones in a purge or evacuation/reduction cycle. The control system may be further configured to operate the reactors in the dehydrogenation cycle in staggered cycles, such that the purge cycle, regeneration cycle, or evacuation/reduction cycle of the reactors in each of the reaction zones do not overlap.

In another aspect, embodiments disclosed herein relate to a process for producing olefins. The process may include: dehydrogenating propane in a first dehydrogenation reaction zone to produce a first effluent comprising propylene; and dehydrogenating isobutane in a second dehydrogenation reaction zone to produce a second effluent comprising isobutene. The first effluent may be cooled in an indirect heat exchanger to produce steam and a cooled first effluent, and the second effluent may be cooled in an indirect heat exchanger to produce steam and a cooled second effluent. The propane fed to the first dehydrogenation reaction zone may be heated via indirect heat exchange with the cooled first effluent, and the isobutane fed to the second dehydrogenation reaction zone may be heated via indirect heat exchange with the cooled second effluent. The first and second effluents may then be compressed, mixed and fed to a common separation train to recover an ethylene fraction, a propylene fraction, a propane fraction, at least one C4 fraction, and one or more fractions including heavy byproducts. In some embodiments, the process may include feeding n-butane to the second dehydrogenation reaction zone to produce the second effluent comprising isobutene and butadiene.

Other aspects and advantages will be apparent from the following description and the appended claims.

BRIEF DESCRIPTION OF DRAWINGS

FIG. 3 is a cycle sequencer display illustrating cyclic operations of a ten-reactor system co-producing propylene and isobutene according to embodiments disclosed herein.

DETAILED DESCRIPTION

Embodiments disclosed herein relate generally to an improved process for the co-production of olefins, including propylene, isobutene, n-butenes, and in some embodiments isopentene; an improved process for the co-production of diolefins, including butadiene and isoprene; and a new integrated process for the co-production of olefins and diolefins, including propylene, isobutene, n-butenes, butadiene, and in some embodiments isopentene and isoprene. More specifically, embodiments herein relate to an integrated process for the co-production of C3 olefins, C4 olefins and diolefins, and C5 olefins and diolefins.

Processes for producing olefins according to embodiments herein may include dehydrogenating propane in a first dehydrogenation reaction zone to produce a first effluent including propylene, unreacted propane, and any light byproducts that may form as a result of cracking, as well as any heavy byproducts that may form as a result of oligomerization. Isobutane may be dehydrogenated in a second dehydrogenation reaction zone, with minimal (such as less than 1 wt % or impurity amounts) or no feed of n-butane to the second dehydrogenation zone, to produce a second effluent including isobutene, unreacted isobutane, as well as light and heavy byproducts. The effluents may then be combined and compressed, or alternatively compressed separately, and fed to a common separation train to recover the desired products, which may include propylene and isobutene, as well as other fractions resulting from incomplete or side reactions.

In some embodiments, propane may be dehydrogenated in the first dehydrogenation reaction zone and n-butane may be dehydrogenated in the second dehydrogenation reaction zone, with minimal (such as less than 1 wt % or impurity amounts) or no feed of isobutane to the second dehydrogenation zone to produce a second effluent including butadiene and/or n-butenes, unreacted n-butane, as well as light and heavy byproducts. In such embodiments, operation of the second dehydrogenation reaction zone may be optimized for the conversion of n-butane to butadiene/n-butenes. In such embodiments, operation of the second dehydrogenation reaction zone may be optimized for maximum production of butadiene and minimum production of n-butenes, or maximum production of n-butenes and minimum production of butadiene, or any mixture of butadiene and n-butenes between these limits.

In other embodiments, propane may be dehydrogenated in the first dehydrogenation reaction zone and a mixture of isobutane and n-butane may be dehydrogenated in the second dehydrogenation reaction zone. In such embodiments, operation of the second dehydrogenation reaction zone may be at conditions suitable for the conversion of isobutane to isobutene or at conditions suitable for the conversion of n-butane to butadiene and/or n-butene.

In other embodiments, isobutane may be dehydrogenated in the first dehydrogenation reaction zone and n-butane may be dehydrogenated in the second dehydrogenation reaction zone. In such embodiments, operation of the first dehydrogenation reaction zone may be at conditions suitable for the conversion of isobutane to isobutene and operation of the second dehydrogenation zone may be at conditions suitable for conversion of n-butane to butadiene and/or n-butenes.

Should co-production of propylene, isobutene, and butadiene/n-butenes be desired, the process may also include feeding propane to a first dehydrogenation reaction zone, isobutane to a second reaction zone, and n-butane to a third dehydrogenation reaction zone to produce a first effluent including propylene and unreacted propane, a second effluent containing isobutene and unreacted isobutane, and a third effluent including butadiene, n-butenes and unreacted n-butane. The first, second and third effluents may be separately or collectively compressed, and fed to the common separation train for recovery of the desired product and recycle fractions, including a propylene fraction, an isobutene fraction, a butadiene fraction, and/or an n-butene fraction.

In yet other embodiments, such as where C5's are also processed, the process may include dehydrogenating isopentane in a second, third or fourth dehydrogenation reaction zone to produce a second, third or fourth effluent comprising isopentene and/or isoprene. During the dehydrogenation cycle, over time, heat is absorbed from the catalyst beds by the endothermic reaction as dehydrogenation proceeds, gradually reducing the temperature of the catalyst bed. This temperature reduction, coupled with coke deposited on the catalyst, decreases its ability to produce the desired products. To remove coke and to restore the necessary heat to the catalyst bed, periodic reheat of the catalyst with hot air is required. As such, each dehydrogenation reaction zone may include two or more reactors operating in parallel, where one reactor may be producing olefins and/or diolefins while the other reactor is being purged, and the catalyst regenerated and reheated to a desired reactor temperature before being brought back on line for olefin and/or diolefin production.

Cyclic operation of the reactors in the individual reaction zones provides some optimization of the process, increasing overall on-stream time. Embodiments herein may be further enhanced by integrating the cyclic operation of the reactors in each of the reaction zones; the regeneration equipment (air compressor, air heater, piping, valving, etc.) may be in parallel to each of the reactors, not just to the reactors in a particular reaction zone. In this manner, the air, steam, and inert supply systems may be sized for a minimal number of reactors, decreasing capital and operating costs of the overall system.

For example, each of the first and second dehydrogenation reaction zones may include two dehydrogenation reactors. Cyclic operation of the reactors may include: operating one reactor in each of the reaction zones in a dehydrogenation cycle; operating one reactor in a regeneration cycle; and operating one reactor in a purge or evacuation/reduction cycle. The dehydrogenation cycles of the two reactors may also be staggered.

Cyclic operation, as described above, result in the four reactors being operated such that there is no overlap in the respective steam purge cycles, there is no overlap in the respective reheat/regeneration cycles, and there is no overlap in the respective evacuation/reduction cycles. Operation of the reactors in the dehydrogenation cycle is staggered, such that the purge cycle, regeneration cycle, or evacuation/reduction cycle of the reactors do not overlap (i.e., no two reactors are being purged at the same time, no two are regenerating at the same time, and no two are being evacuated/reduced at the same time). This facilitates the use of common reactor cyclical equipment for supply of steam, air, and inerts.

Such a cyclic operation also results in the ability to properly size and control the recovery of hydrocarbons during a steam purging cycle. For example, prior to compressing the second effluent, an effluent stream including steam and hydrocarbons from a reactor undergoing a purge cycle may be combined with the second effluent, from the C4 dehydrogenation reactor. Purge steam is subsequently removed by condensation in downstream product compressor inter-stage coolers.

To facilitate the cyclic operations, processes herein may include sequentially operating two or more valves, disposed in a parallel flow arrangement, for providing air, steam, and inerts, as required, from the common regeneration system to the reactors in the reheat/regeneration cycle and the reactor in the purge/evacuation/reduction cycle, and for providing propane, n-butane, and isobutane, as required, to the reactors in the dehydrogenation cycle.

Figure 1:
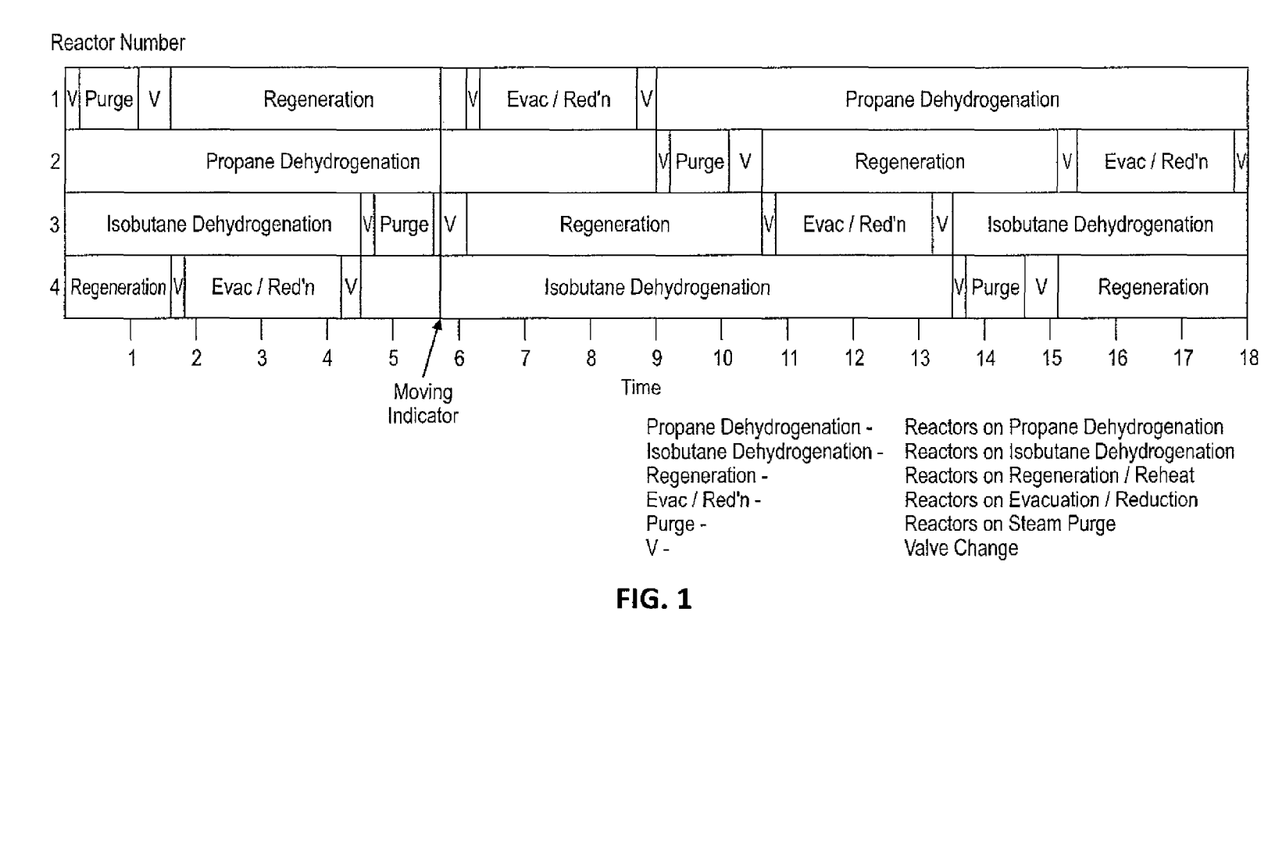
FIG. 1 is a cycle sequencer display illustrating cyclic operations of a four-reactor system co-producing propylene and isobutene according to embodiments disclosed herein.

The above-described cyclic operations encompassing multiple reaction zones are illustrated in FIG. 1, where the system includes four reactors—reactors 1 and 2 are propane dehydrogenation reactors, and reactors 3 and 4 are isobutane dehydrogenation reactors.

Figure 2:
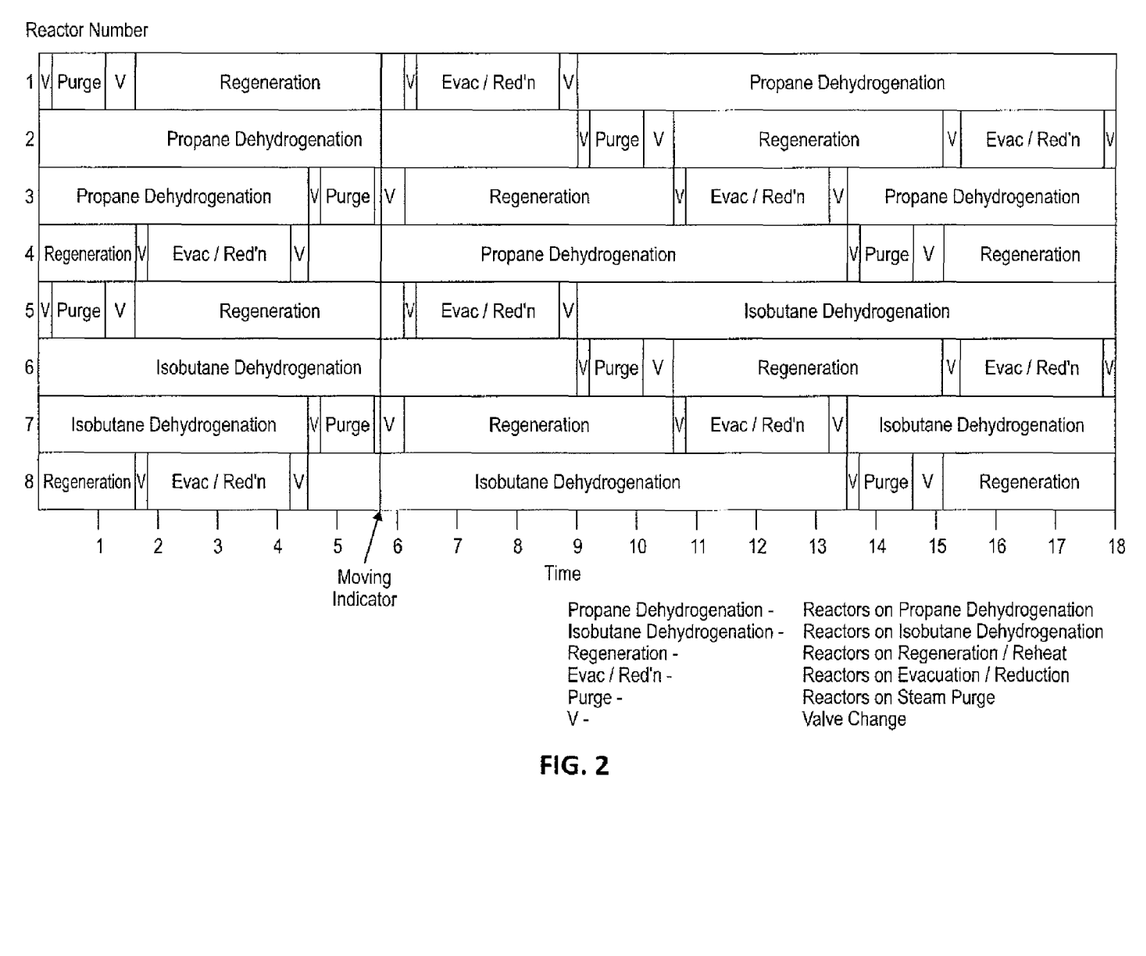
FIG. 2 is a cycle sequencer display illustrating cyclic operations of an eight-reactor system co-producing propylene and isobutene according to embodiments disclosed herein.

While described for a four reactor system (two reaction zones, two reactors each) above, similar cyclic operations may be performed in an eight reactor system (two reaction zones, four reactors each), as illustrated in FIG. 2. Where each of the first and second dehydrogenation reaction zones include four reactors, the process may include: operating two reactors in each of the reaction zones in a dehydrogenation cycle; operating one reactor in each of the reaction zones in a regeneration cycle; and operating one reactor in each of the reaction zones in a purge or evacuation/reduction cycle.

In the eight reactor system, two reactors, one in each reaction zone, may have overlapping sequences (reactors 1 and 5, reactors 2 and 6, etc.), but no two reactors in the same reaction zone have overlapping purge cycles, regeneration cycles, or evacuation/reduction cycles (i.e., no two reactors in the same reaction zone, propane dehydrogenation reaction zone or isobutane dehydrogenation reaction zone, are being purged at the same time, no two are regenerating at the same time, and no two are being evacuated/reduced at the same time).

While described for a four reactor system (two reaction zones, two reactors each) above, similar cyclic operations may be performed in a ten reactor system (two reaction zones, five reactors each), as illustrated in FIG. 3. Where each of the first and second dehydrogenation reaction zones include five reactors, the process may include: operating two reactors in each of the reaction zones in a dehydrogenation cycle; operating two reactors in each of the reaction zones in a regeneration cycle; and operating one reactor in each of the reaction zones in a purge or evacuation/reduction cycle.

In the ten reactor system, two reactors, one in each reaction zone, may have overlapping sequences (reactors 1 and 6, reactors 2 and 7, etc.), but no two reactors in the same reaction zone have overlapping purge cycles or evacuation/reduction cycles (i.e., no two reactors in the same reaction zone, propane dehydrogenation reaction zone or isobutane dehydrogenation reaction zone, are being purged at the same time, and no two are being evacuated/reduced at the same time). In the ten reactor system, two reactors in each zone are under regeneration, but staggered in relation to the start of the cycle.

Embodiments herein also relate to systems for producing olefins and diolefins, including propylene, isobutene, and in some embodiments n-butenes/butadiene, and in other embodiments isopentene and isoprene. The system may include a first dehydrogenation reaction zone for dehydrogenating propane to produce a first effluent including propylene. The system also includes a second dehydrogenation reaction zone for dehydrogenating at least one of isobutane and n-butane to produce a second effluent including at least one of isobutene and n-butenes/butadiene, respectively. One or more compressors, having one or more compression stages each, may be used for compressing the first effluent and the second effluent. A common separation train may be provided for separating the first and second effluents to recover a propylene fraction, a propane fraction, at least one C4 fraction, and one or more fractions including light byproducts and heavy byproducts.

Flow conduits, pumps, valves, and other components and associated equipment may be provided for transporting the feeds, effluents, products, purges, and recycle streams between apparatus in the system. For example, in some embodiments, n-butane is dehydrogenated in the second dehydrogenation reaction zone, with minimal (such as less than 1 wt % or impurity amounts) or no feed of isobutane to the second dehydrogenation zone.

In other embodiments, for example, isobutane is dehydrogenated in the second dehydrogenation reaction zone, with minimal (such as less than 1 wt % or impurity amounts) or no n-butanes fed to the second dehydrogenation reaction zone. In such embodiments, should production of n-butenes/butadiene also be desired, the system may also include a third dehydration reaction zone and flow conduits for feeding n-butane to a third dehydrogenation reaction zone to produce n-butenes/butadiene.

As described above, processes herein may include cyclic operations. Systems according to embodiments herein may include a control system configured for: operating one reactor in each of the reaction zones in a dehydrogenation cycle; operating one reactor in a regeneration cycle; and operating one reactor in a purge or evacuation/reduction cycle. The control system may be further configured for sequentially operating two or more valves disposed in a parallel flow arrangement for providing air, steam, and inerts, as required, from a common regeneration system to the reactors in the reheat/regeneration cycle and the reactor in the purge/evacuation/reduction cycle, and for providing propane, n-butane, and isobutane, as required, to the reactors in the dehydrogenation cycle. The control system, in other words, may be configured to operate the reactors in the dehydrogenation cycle in staggered cycles, such that the purge cycle, regeneration cycle, or evacuation/reduction cycle of the reactors do not overlap.

Prior to compressing the second effluent, an effluent stream including steam and hydrocarbons from a reactor undergoing a purge cycle may be combined with the second effluent, from the C4 dehydrogenation reactor. A mixing device, such as a vessel, a mixing tee, a pump, or other apparatus for mixing of streams, may be provided for combining the effluent including steam and hydrocarbons from a reactor in a purge cycle with the effluent from a dehydrogenation reaction zone reactor operating in a dehydrogenation cycle. Purge steam is subsequently removed by condensation in downstream product compressor inter-stage coolers.

The separation zone for separating the combined effluents may include one or more distillation columns and/or extractive distillation units and/or reaction units for separation and recovery of the various product fractions, recycle fractions, and byproduct fractions. For example, when producing isobutene and propylene, the separation system may include a deethanizer, a depropanizer, a C3 splitter, and a C4 splitter; in some embodiments, an isobutene reaction unit may be used in lieu of or in addition to the C4 splitter. In some embodiments, the separation system may include a deoiler, separating C5+ heavies from the C4's, which may be recycled as a whole to the C4 dehydrogenation reaction zone. In some embodiments, the isobutene from the C4 splitter or in the isobutene reaction unit may be converted in an etherification reactor to produce an ether product, such as MTBE or ETBE. When producing normal butenes, the separation system may include a selective olefin extraction unit. When producing butadiene, the separation system may also include a butadiene extraction unit. In yet other embodiments, the separation system may include a light ends recovery unit, such as for separation of methane and hydrogen, which may be separated and recovered via pressure swing adsorption or may be used as a fuel gas for various unit operations, including as a fuel feedstock to a charge heater heating the propane and isobutane feeds upstream of the hydrogenation reaction zones. Other various options are described further below.

The system may further include heat integration, heating various feed streams and column reboiler streams, cooling column overheads streams and reactor effluent streams, etc., to recover heat and/or produce steam, reducing the overall external duty requirements for the plant. For example, one or more heat exchangers may be provided for recovering heat from at least one of the first effluent and the second effluent.

Figure 4:
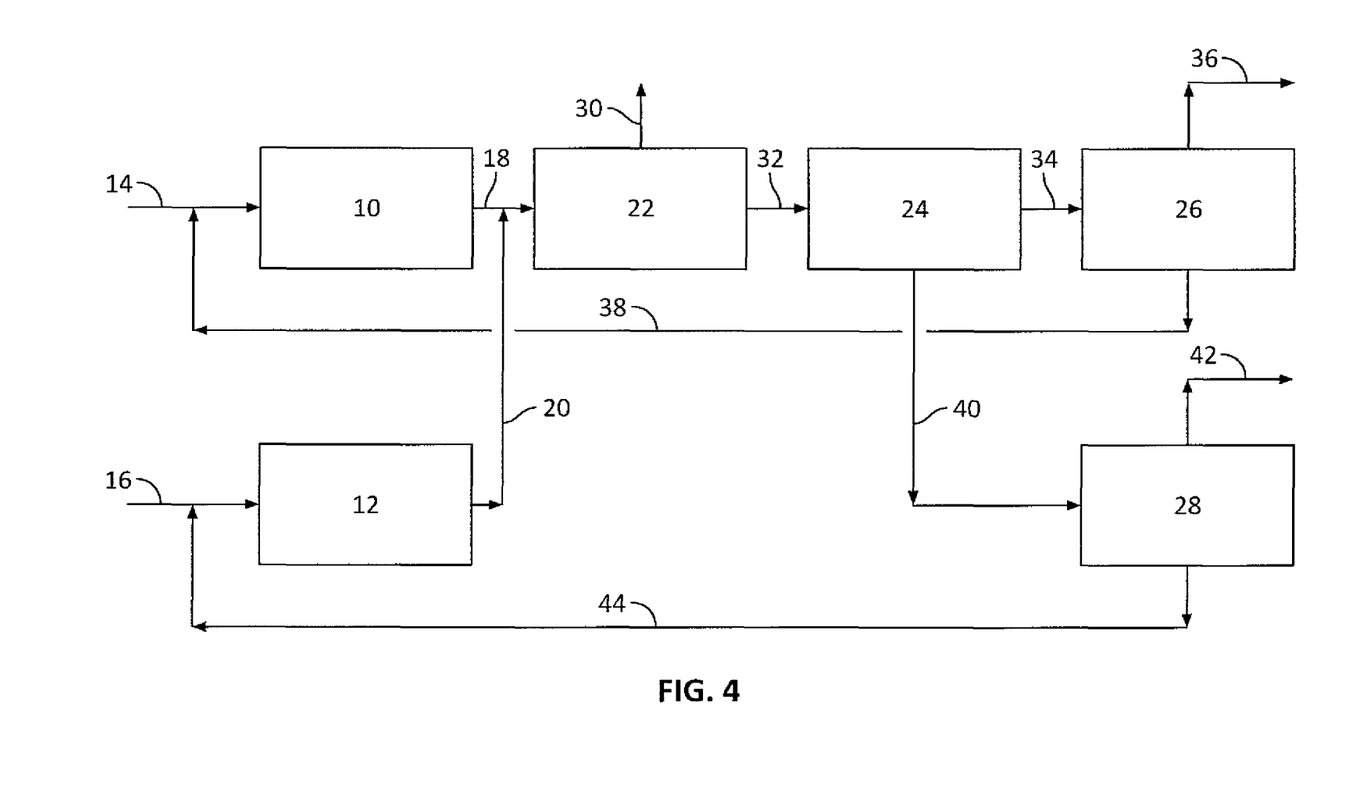
FIG. 4 is a block flow diagram of a process for the co-production of propylene and isobutene according to embodiments herein.

Referring now to FIG. 4, a block flow diagram of a process according to embodiments herein is illustrated. The process of FIG. 4 includes a first dehydrogenation reaction zone 10 and a second dehydrogenation reaction zone 12. Propane may be fed via flow line 14 to first dehydrogenation reaction zone 10, and isobutane may be fed vial flow line 16 to second dehydrogenation reaction zone 12.

First dehydration reaction zone 10 may contain a dehydrogenation catalyst suitable for converting propane to propylene, and may be operated at reaction conditions selected for conversion of propane to propylene. Second dehydration reaction zone 12 may contain a dehydrogenation catalyst suitable for converting isobutane to isobutene, which may be the same or different than the catalyst in the first dehydration reaction zone 10, and may be operated at reaction conditions selected for conversion of isobutane to isobutene, which may be the same or different than the operating conditions in the first dehydration reaction zone 10.

An effluent 18 may be recovered from the first dehydration reaction zone 10, including the desired reaction product, propylene, unreacted propane, and any reaction byproducts. An effluent 20 may be recovered from the second dehydration reaction zone 12, including the desired reaction product, isobutene, unreacted isobutane, and any reaction byproducts.

The effluents may then be sent to a separation system, which as illustrated, may include a deethanizer 22, a depropanizer 24, a C3 splitter 26, and an isobutene reaction unit 28 (e.g., MTBE unit). Ethylene, methane, and/or hydrogen, as well as other light byproducts, may be separated from the C3 and heavier components in deethanizer 22, the light ends being recovered via flow line 30, and the C3+ components being recovered via flow line 32. In depropanizer 24, the C3's may be separated from the C4's. The C3's may be fed via flow line 34 to C3 splitter 26, recovering an overhead product propylene fraction 36 and a bottoms recycle propane fraction 38, which may be recycled to dehydrogenation reaction zone 10. The C4's may be fed via flow line 40 to isobutene reaction unit 28, reacting isobutene to produce products such as a MTBE or ETBE fraction 42 and a recycle isobutane fraction 44, which may be recycled to dehydrogenation reaction zone 12. A purge stream (not illustrated) may also be provided to avoid excessive buildup of C5+ heavies in the system.

Figure 5:
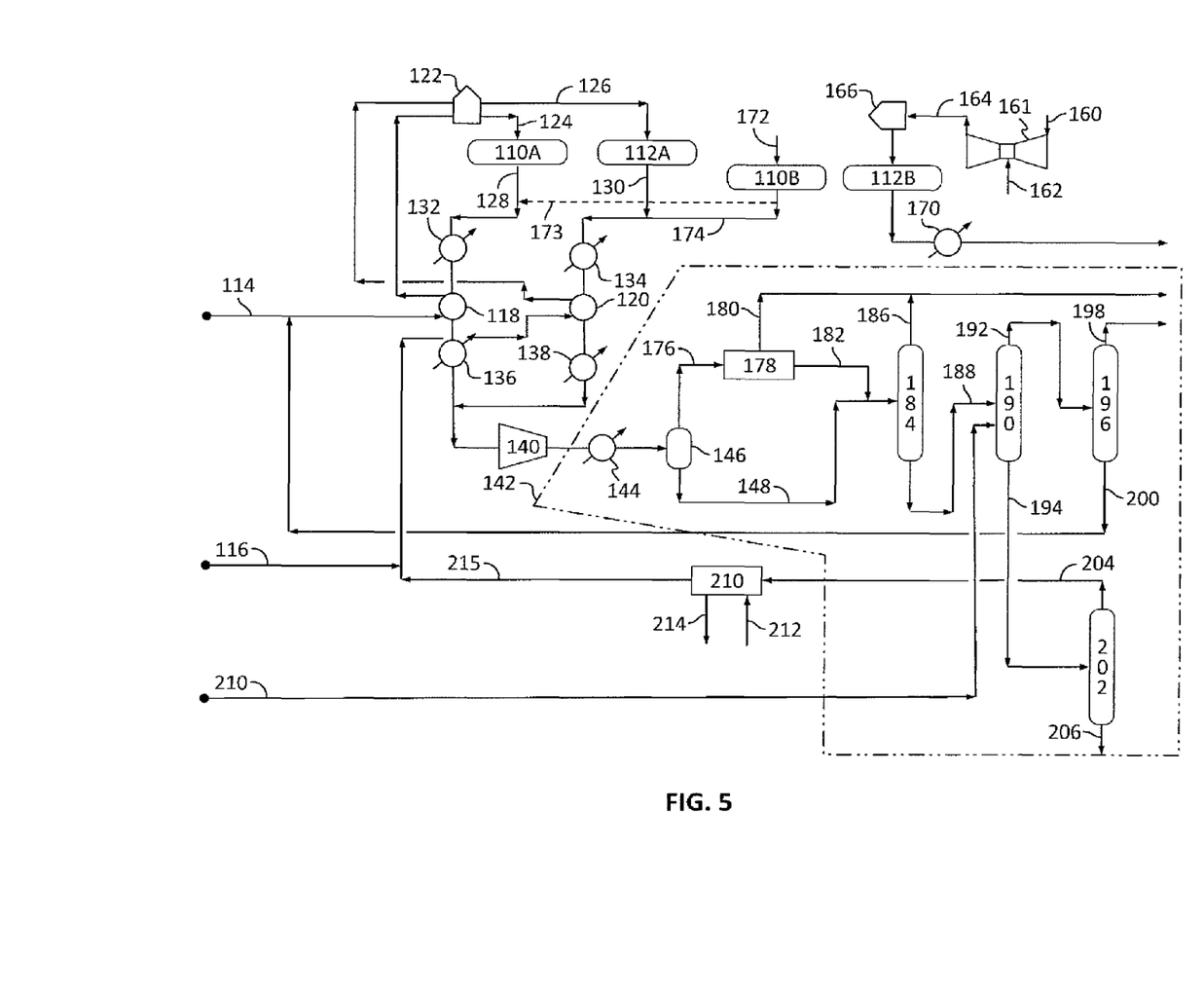
FIG. 5 is a simplified process flow diagram of a process for the co-production of propylene, isobutene and butadiene according to embodiments herein.

Referring now to FIG. 5, a simplified process flow diagram of a process for converting propane and isobutane to olefins is illustrated. The system as illustrated in FIG. 5 includes two reaction zones, a C3 dehydrogenation reaction zone 110, and a C4 dehydrogenation reaction zone 112, each including two reactors in parallel (110A, 110B, 112A, and 112B). During the cyclic operation of the reactors, at any given time there is one reactor in C3 dehydrogenation service (110A), one reactor in C4 dehydrogenation service (112A), and two reactors (110B, 112B) being prepared for dehydrogenation service, where reactors 110B and 112B are in different cycles (purge, regeneration/reheat, evacuation/reduction).

Propane feedstock may be introduced to the system via flow line 114. Isobutane feedstock may be introduced to the system via flow line 116. The propane and isobutane feedstocks may then be preheated, such as via feed-effluent exchangers 118, 120, respectively, and a charge heater 122, and the heated streams 124, 126 fed to the C3 and C4 dehydrogenation reactors 110A, 112A, respectively.

The propane and isobutane feedstocks may then be converted in the dehydrogenation reaction zone to olefins. A C3 dehydrogenation effluent may be recovered from reactor 110A via flow line 128, and a C4 dehydrogenation effluent may be recovered from reactor 112A via flow line 130. The effluents may be cooled via indirect heat exchange, such as for production of steam in one or more heat exchangers 132, 134, for heating of feeds in heat exchangers 124, 126, and any additional coolers 136, 138 as may be necessary to reduce the effluent to a desired temperature prior to further processing.

As illustrated in FIG. 5, reactor 112B is in a reheat cycle. During the reheat cycle, air 160 is compressed in air compressor 161 and heated in an air heater 166 and passed through reactor 112B, re-heating the catalyst to a desired temperature and burning off any coke that may have formed on the catalyst. The reheat effluent 168 may then be used to produce steam via heat exchanger 170, if desired.

As also illustrated in FIG. 5, reactor 110B is in a purge cycle. During the purge cycle, steam 172 is passed through reactor 110B, stripping residual hydrocarbons from the catalyst bed. The purge effluents 173, 174 may be combined with the C3 or C4 dehydrogenation effluents 128, 130, respectively, for collective recovery of the residual hydrocarbons with the dehydrogenation reactor effluents.

The C3 and C4 dehydrogenation effluents 128, 130, as well as the purge effluents 173, 174, may be compressed in a compressor 140, to facilitate separation of the components in separation zone 142. Compressor system 140 may include one or more compression stages, intercoolers, and interstage knock-out drums (each not shown). For example, any water that may condense after each compression stage, such as may be present from the steam purge, may be separated in the interstage knock-out drums.

Separation zone 142 may include a cooler 144 and/or a flash drum 146, to reduce a temperature of the compressor effluent and separate condensed heavies 148 from the compressor effluent. Vapor 176 from flash drum 146 may be dried and sent to a low temperature recovery unit (LTRU) 178, where C3+ hydrocarbons are recovered by chilling and condensing. The non-condensable components are recovered via flow line 180, and the condensed hydrocarbons 182 are combined with the liquids 148 from flash drum 146 and sent to deethanizer 184.

Deethanizer 184 may be used to separate an overheads fraction 186, which may include ethane and ethylene, for example, from a bottoms fraction 188, which includes the C3+ hydrocarbons. Bottoms fraction 188 may then be fed to a depropanizer 190 for separation of the C3s, recovered in overheads 192, from the C4+ hydrocarbons, recovered in bottoms 194. The C3s may then be separated in C3 splitter 196 to recover a propylene product fraction 198 and a propane recycle fraction 200. The C4s may be separated from heavies in a deoiler 202, the recycle C4s recovered as an overheads fraction 204, and heavies being recovered as a bottoms fraction 206.

As described above, the propane and isobutane feeds may be fed as individual streams to the reaction system. Alternatively or additionally, propane and isobutane may be fed as a mixed stream 210, such as where a mixture of C3 and C4 hydrocarbons is readily available, to the separation zone for separation into the respective feedstocks. In such embodiments, the reactants, such as propane and isobutane, are not simultaneously processed in a single reactor.

In some embodiments, it may be desired to convert the isobutene to an ether, such as for use as a gasoline additive. As illustrated in FIG. 5, the C4 recycle fraction may be fed to an etherification reaction zone 210 to react the isobutene with an alcohol 212, such as methanol, to form an ether 214, such as MTBE, prior to recycle of the remaining C4s in stream 215 to the dehydrogenation reaction zone.

Figure 6:
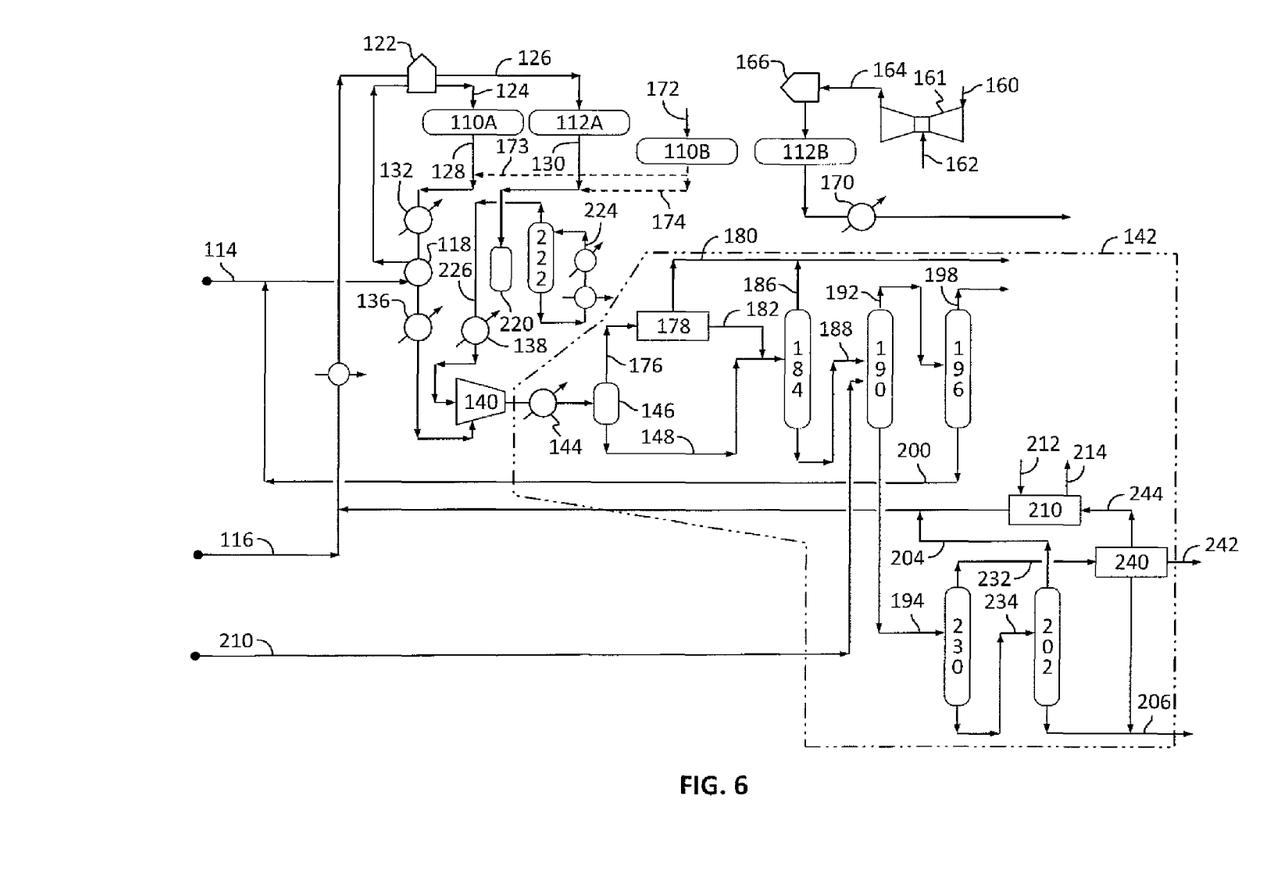
FIG. 6 is a simplified process flow diagram of a process for the co-production of propylene, isobutene, n-butenes and butadiene according to embodiments herein.

Referring now to FIG. 6, a simplified process flow diagram of a process for converting propane, n-butane, and isobutane to olefins and dienes is illustrated, where like numerals represent like parts. In this embodiment, isobutane and n-butane may be fed via flow line 116 to the C4 dehydrogenation reaction zone 112. Alternatively or additionally, the isobutane and n-butane may be fed in a C3/C4 mixture via flow line 210 to separation zone 142.

The isobutane and n-butane may be heated, as described above, and fed to the C4 dehydrogenation reactor 112A, forming a reaction product including n-butenes, isobutene, butadiene, and unreacted feeds. Due to the presence of butadiene, and polymeric reaction byproducts, the effluent 130 from the C4 dehydrogenation reactor may be fed to a pre-quench tower 220, and a main quench tower 222, where the vapor is cooled by direct contact with a circulating quench oil stream 224. Polymeric compounds in reactor effluent 130 are absorbed by the quench oil. The vapor portion 226 may then be forwarded to the compression section of the plant and processed as described above.

Similar to the process as described with respect to FIG. 5, separation zone 142 may include a cooler 144, a flash drum 146, an LTRU 178, a deethanizer 184, a depropanizer 190, and a C3 splitter 196. The C4+ fraction 194 recovered from the depropanizer 190 may then be fed to a prefractionator 230, for an initial separation of the light C4s as an overheads fraction 232, including butadiene, n-butenes, and isobutene, from a bottoms fraction 234, including heavy C4s and C5+ hydrocarbons. The light C4 fraction 232 may then be processed in a butadiene extraction unit 240 to recover a butadiene product stream 242 and a C4 olefin product stream 244. The bottoms fraction 234 may be fed to a deoiler 202, separating recycle C4s 204 from heavies 206. In this embodiment, if desired, the isobutene in the C4 olefin product stream may be reacted in the etherification reaction zone 210 to produce ethers 214.

Figure 7:
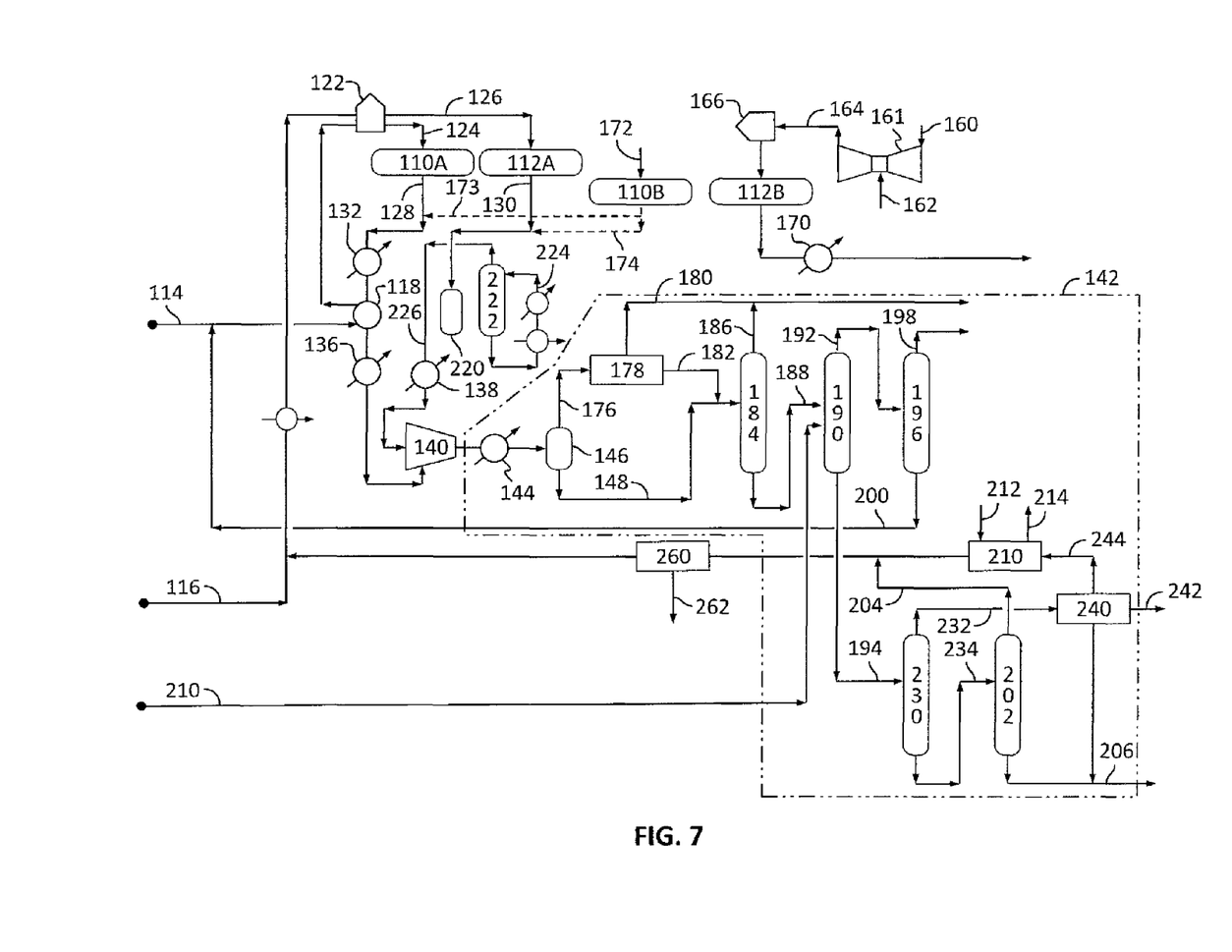
FIG. 7 is a simplified process flow diagram of a process according to embodiments herein.

Referring now to FIG. 7, a simplified process flow diagram of a process for converting propane, n-butane, and isobutane to olefins and dienes is illustrated, where like numerals represent like parts. In this embodiment, the feedstocks may be processed in a manner similar to that as described with respect to FIGS. 4 and 5. Additionally, the recycle C4 stream may be processed in a selective olefin extraction unit 260 to recover an n-butene product stream 262.

As described above, embodiments herein relate to a process for simultaneously dehydrogenating propane and isobutene to produce a mixed stream of propylene and isobutene, inerts (H2, CO and CO2), cracked by-products (CH4, C2H4 and C2H6) and unreacted feed (propane and isobutane). Separate C3 and C4 dehydrogenation reactors are dedicated for the separate C3 and C4 feedstocks, such that, in some embodiments, propane, n-butane, and isobutane feeds are not simultaneously processed in a single reactor, for example. The reactor effluents are combined and processed in a common product compressor train, low temperature recovery unit (LTRU), and distillation train. High-purity propylene and isobutene-rich products are separated. Concentrated propane and isobutane streams are separately recycled to their respective dehydrogenation reactors. In some embodiments, n-butane may be co-processed with isobutane in the C4 dehydrogenation reactor, and a separate butadiene product can be obtained. Depending on the amounts of isobutane and n-butane in the feeds, separate dehydrogenation reactors may be utilized in some embodiments.

Embodiments herein provide a low investment cost means of dehydrogenating: separate propane, isobutane and/or n-butane feedstocks; a combined propane/isobutane feedstock; separate propane and combined isobutane/n-butane feedstocks; or a combined propane/isobutane/n-butane feedstock. Processes herein may include a separate feed vaporization systems for each feed. In some embodiments, isobutane and n-butane feeds may be combined. Separate charge heaters, or a single combined charge heater, may be employed.

Cyclical fixed-bed dehydrogenation reactors are employed. As an example, a four-reactor configuration could be utilized with two reactors on hydrocarbon (HC) cycle, one reactor on air reheat/regeneration cycle, and one reactor on steam purge/evacuation/reduction cycle. Air reheat/regeneration equipment may be shared. The four-reactor system would be segregated, with two reactors only used to convert propane and two reactors only used to convert isobutane. In this manner, the catalyst can be optimized for the individual HC feeds. Unconverted propane, isobutene and/or n-butane are separated from the dehydrogenation products, and mixed with separate fresh propane, fresh isobutane and/or fresh n-butane feeds, then fed to the C3 dehydrogenation and C4 dehydrogenation reactors, respectively.

Embodiments disclosed herein, integrating the C3/iC4 and/or nC4 dehydrogenation processes have several advantages over separate C3 dehydrogenation, iC4 dehydrogenation, and n-C4 dehydrogenation units when producing the same propylene, isobutene and butadiene products.

Processes herein include a single dehydrogenation reactor train, although the propylene reactors are segregated from the isobutene reactors in terms of feedstock, catalyst and reaction conditions. Propane is fed only to the dedicated propylene reactors and isobutane is fed only to the dedicated isobutene reactors.

Processes disclosed herein provide flexibility in processing: in the case of n-butane processing, n-butane may be sent together with isobutene to the C4 dehydrogenation reactors or separate from isobutane to dehydrogenation reactors, depending on the amounts of isobutane and n-butane in the feed. In the case of separate butadiene production, propylene may be sent together with isobutane to the same dedicated C3/iC4 dehydrogenation reactors.

Although the propylene and isobutane/n-butane reactors are dedicated, the cyclical operation of the dehydrogenation reactor train operates in the same fashion as if there were only a single hydrocarbon feedstock. Only the hydrocarbon feed and hydrocarbon outlet piping are different. As another advantage, all other reactor cyclical operations and equipment are common, including: steam purge cycle, reheat/regeneration cycle, evacuation/reduction cycle.

Further, the reactor effluents are combined and processed in a common compression, lights recovery and distillation train. Unreacted propane and isobutane are recycled to the respective propylene and isobutene reactors.

Reactor conditions (catalyst, catalyst loading, space velocity, hydrocarbon feed temperature, air/hydrocarbon ration, air temperature, etc.) can be optimized for the separate dedicated reactors. This results in economies of scale and elimination of all duplicated equipment items in the case of separate C3 dehydrogenation and iC4 dehydrogenation units. There is one unit instead of two units. The equipment piece count is far less with one unit than with two. There is only one product compression train.

The dehydrogenation processes according to embodiments herein include fixed-bed reactors which operate at low pressure and elevated temperature. Conditions are selected to optimize the complex relationship among conversion, selectivity and energy consumption in the temperature and pressure range of 400 to 750° C. and 0.01 to 1 $kg/cm^2$ absolute, such as from 575-650° C. and 0.1-0.5 $kg/cm^2$ absolute.

Side reactions occurring simultaneously with the main reaction cause the formation of some light hydrocarbon gases and heavy hydrocarbons, as well as the deposition of coke on the catalyst. The overall selectivity of propane to propylene is greater when dehydrogenating propane in a dedicated reaction zone, the overall selectivity of isobutane to isobutene is greater when dehydrogenating isobutane in a dedicated reaction zone, and the overall selectivity of n-butane to n-butenes/butadiene is greater when dehydrogenating n-butane/n-butenes in a dedicated reaction zone compared with selectivities that can be achieved when co-processing combinations of propane, isobutane and n-butane in the same reaction zone. In some embodiments, the overall selectivity of propane to propylene may be greater than 88 mole %, the overall selectivity of isobutane to isobutene may be greater than 90 mole %, and the overall selectivity of n-butane to n-butenes/butadiene may be greater than 60 mole %.

Heat absorbed from the catalyst bed by the reaction as dehydrogenation proceeds gradually reduces the temperature of the catalyst bed. This temperature reduction, coupled with coke deposited on the catalyst decreases its ability to produce the desired products. To remove coke and to restore the necessary heat to the catalyst bed, periodic reheat of the catalyst with hot air is required.

The C3 dehydrogenation reactor effluent is routed through a high pressure steam generator, feed-effluent exchanger and trim cooler to a compressor. The iC4 dehydrogenation reactor effluent is also routed through a high pressure steam generator, feed-effluent exchanger and trim cooler to the compressor. The compressor discharge is partially condensed in the final aftercooler. The vapor and liquid are separated in a flash drum and the vapor is sent to the low temperature recovery unit to recover C3 s and C4s. These hydrocarbons are combined with liquid from the flash drum and sent to a deethanizer.

The process is carried out in a train of fixed-bed reactors that operate on a cyclic basis and in a defined sequence to permit continuous uninterrupted flow of the major process streams. In one complete cycle, hydrocarbon vapors are dehydrogenated and the reactor is then purged with steam and blown with air to reheat the catalyst and burn off the small amount of coke that is deposited during the reaction cycle. These steps are followed by an evacuation and reduction and then another cycle is begun.

Cycle timing instrumentation sequences the actuation of hydraulically operated valves to control the operation. The system may be suitably interlocked to ensure safe operation of the valves in sequence and prevent mixing of air and hydrocarbon gas.

In the reaction section, propane is converted to propylene, isobutane is converted to isobutene, and n-butane, when present, is converted to n-butenes and butadiene while passing through a catalyst bed. Separate dedicated C3 dehydrogenation reactors are used for the propane to propylene conversion and separate dedicated C4 dehydrogenation reactors are used for the isobutane to isobutene conversion.

N-butane conversion to n-butene/butadiene can be in separate dehydrogenation reactors or combined with isobutene to isobutene conversion in the C4 dehydrogenation reactors. Alternatively, in the case of n-butane conversion to n-butene/butadiene in dehydrogenation reactors, propane to propylene conversion may be combined with isobutene to isobutene conversion in the dehydrogenation reactors.

In the C3 dehydrogenation reactors, the fresh propane feed is combined with recycle feed from the bottom of the C3 splitter. The resulting stream is vaporized by heat exchange with various process streams. The vaporized total propane feed is then heated by exchange with the reactor effluent in a propylene reactor feed—effluent exchanger. Upstream of this exchanger, a small quantity of dimethyl disulfide may be added to the feed to passivate metals in the alternating oxidating and reducing atmosphere of the reactors.

The total C3 feed is then raised to reaction temperature in the gas fired charge heater and sent to the propylene dehydrogenation reactors. Non-selective cracking of hydrocarbons may be minimized by injecting fuel gas during the reheat portion of the cycle to keep the heater outlet temperature as low as possible. Hot effluent from the propylene dehydrogenation reactors is cooled by generating steam in a propylene reactor effluent steam generator and by heat exchange with the reactor feed and flows to the compression section of the plant.

In the iC4 dehydrogenation reactors, similarly, fresh isobutane and recycle isobutane (which may be from a downstream MTBE synthesis unit, as described above) are preheated by exchange with various process streams and raised to reaction temperature in a fired heater. The isobutane fired heater box may be common with the propane fired heater box. The heater effluent is charged to the on-stream isobutane dehydrogenation reactors. Small amounts of n-butane can also be processed with isobutane in the C4 dehydrogenation reactors. Hot effluent from the isobutene dehydrogenation reactors is cooled by generating steam in an isobutane dehydrogenation reactor effluent steam generator and by heat exchange with the reactor feed and flows to the compression section of the plant.

In the n-C4 dehydrogenation reactors, when used, such as in the case of significant butadiene production, separate and dedicated dehydrogenation reactors can be utilized. Fresh n-butane feed is combined with recycle butane and butenes from a downstream butadiene extraction unit. The total feed is then vaporized by heat exchange with a circulating quench oil stream. Upstream of this exchanger, a small quantity of a sulfiding agent may be added to the feed to passivate metals in the alternating oxidating and reducing atmosphere of the reactors. The total feed is then brought to reaction temperature in the gas fired charge heater, which may be common with the propane and iC4 fired heater box, and sent to the reactors.

Hot effluent from the reactors flows to a pre-quench tower and a main quench tower, where the vapor is cooled by direct contact with a circulating quench oil stream. Polymeric compounds in the reactor effluent are absorbed by the quench oil. In order to maintain the properties of the quench oil, a slipstream may be withdrawn and charged to a quench oil vaporizer. Steam may be injected and the stream is partially vaporized. The vapor portion is returned to the system and the heavy liquid is rejected. Make-up quench oil may be added intermittently to maintain system inventory. Main quench tower overhead is cooled and flows to the compression section of the plant.

After the dehydrogenation reaction cycle, while the reactor system is still under vacuum, the reactor may be thoroughly purged with steam, thereby stripping residual hydrocarbons from the catalyst and reactor into the recovery system. Reheat of the catalyst may be conducted at slightly above atmospheric pressure. Reheat air is supplied typically by a gas turbine or air compressor and heated to the required temperature in a direct-fired duct burner before passing through the reactors. The reheat air serves to restore both the temperature profile of the bed to its initial on-stream condition and catalyst activity, in addition to burning the coke off the catalyst. The reheat air leaving the reactors may be used to generate steam in a waste heat boiler.

When the reheat of a reactor is complete, the reactor is re-evacuated before the next on-stream dehydrogenation period. Prior to introducing hydrocarbon feed, hydrogen rich off-gas may be introduced to the reactor for a short time to remove absorbed oxygen from the catalyst bed. This reduction step decreases the loss of feed by combustion and restores the catalytic metal, such as chrome, on the catalyst to its active state. The reheat air stream leaving the reactors flows to the waste heat boiler which may be used to generate and superheat high pressure steam.

The cooled reactor effluent gases from the C3 dehydrogenation reactors, iC4 dehydrogenation reactors, and n-C4 dehydrogenation reactors, when present, may be combined and compressed in a single or multiple product compressors to a suitable level for the operation of the recovery section. For each compression stage, a compression ratio may be selected to optimize compressor performance and keep gas temperature sufficiently low to minimize polymer formation. A separate compression stage (booster compressor) may be used for any butadiene-containing reactor effluent gas, to allow operation of the n-C4 dehydrogenation reactors at a much lower pressure (deeper vacuum) than the other dehydrogenation reactors.

Any water that condenses after each stage of compression may be separated in an interstage knock-out drum. Additionally, a sodium nitrite solution may be circulated in the final stage suction drum as an oxygen scavenger to aid in the prevention of polymer in the downstream gas plant section.

The compressor discharge vapor is cooled and the resulting vapor-liquid is separated in a flash drum. The uncondensed reactor effluent vapor is sent to the low temperature recovery unit (LTRU) and the reactor effluent condensate is sent to the deethanizer in the recovery section.

The recovery section removes inert gases, hydrogen, and light hydrocarbons from the compressed reactor effluent. The propane, propylene, butanes, butenes and heavier components are sent to the product purification section. The vapor from the flash drum is dried and sent to the low temperature recovery system where C3s and C4s are recovered by chilling and condensation. These hydrocarbons are combined with liquid from the flash drum and sent to the deethanizer.

The hydrogen-rich gas from the low temperature recovery section can be sent to a pressure-swing adsorption (PSA) unit to recover hydrogen, if desired. The remaining gas is sent to the reactor section reduction gas surge drum and the facility fuel gas header.

The deethanizer serves to separate the ethane and lighter hydrocarbons from the propane, propylene, butane, butene and heavier material. Uncondensed vapor from the tower overhead is sent to the fuel gas header. The deethanizer bottoms liquid flows forward to the product purification section.

The product purification section is designed to recover a high-purity propylene product from propane and heavier material. It can also be designed to recover a concentrated isobutene/isobutene stream to feed an MTBE unit and to produce a concentrated butadiene stream to feed a butadiene extraction unit.

The deethanizer bottoms fraction from the recovery section is charged to the depropanizer. The depropanizer removes propane and propylene from the butanes, butenes and heavier material. The overhead is sent to the C3 splitter and the bottoms is recovered as product and sent to a MTBE synthesis unit or, in the case of butadiene production, first to a prefractionator and butadiene extraction unit.

The C3 splitter may produce greater than 99.5 wt % propylene as an overhead product. An open loop "heat pump" system may be used to provide reboiler heat. The tower overhead product is pumped through a sulfur removal unit before being sent as high purity propylene product to product storage, a polypropylene unit, or other downstream processing. Bottoms from the C3 splitter may be returned to the C3 dehydrogenation reactors as recycle propane feed.

Depropanizer bottoms may be sent to a pre-fractionator, where butadiene is concentrated in the overhead and sent to a solvent extraction unit, where high-purity 1,3-butadiene is recovered. The pre-fractionator bottoms are fed to a deoiler, where C5+ heavies are removed in the bottoms and normal butane and n-butenes in the overhead are recycled to the dehydrogenation reactors. The raffinate-1 from the butadiene extraction unit is sent to a MTBE unit, where isobutene is removed by reaction, and isobutane is recycled to the iC4 dehydrogenation reactors. Heavies from the deoiler bottoms are cooled and burned as a supplementary fuel in the reactor charge heater.

Recycle normal butane and butenes from the deoiler overhead and raffinate from the MTBE unit can be separated in a selective olefins extraction (SOE) unit to recover a concentrated normal butenes stream to feed an oxidative dehydrogenation unit, a metathesis unit or a polybutenes unit. The separated n-butane stream is then recycled to the n-C4 dehydrogenation reactors.

Embodiments herein may be used for any relative amounts of propylene, isobutene and butadiene production, and at any combination of capacities. Processes herein may be used for producing: propylene and isobutene, propylene and butadiene; isobutene and n-butadiene; propylene, isobutene and butadiene; and at any combination of product rates. In the case of butadiene production, n-butene may be extracted as a co-product. The plant may be designed for "once-thru" operation. In various embodiments, isobutane and n-butane may be processed together in the same dedicated dehydrogenation reactors; alternatively, isobutane and propane may be processed together in the same dedicated dehydrogenation reactors.

Any number of dehydrogenation reactors may be used according to the product capacities. The LTRU and distillation train may be customized based on product slate and capacities.

Reactor conditions can be different for each dehydrogenation reactor during each cycle. Air flow and temperature may be changed during the reheat/regeneration step for each dehydrogenation reactor to maintain overall reactor heat balance. The distillation train may include a deethanizer, depropanizer and C3 Splitter for propylene production. The distillation train may also include a pre-fractionator for butadiene separation. A PSA unit can be added to recover a high-purity hydrogen product from the LTRU offgas. A C2 splitter can be added to recover a high-purity ethylene product.

While the disclosure includes a limited number of embodiments, those skilled in the art, having benefit of this disclosure, will appreciate that other embodiments may be devised which do not depart from the scope of the present disclosure. Accordingly, the scope should be limited only by the attached claims.

What is claimed:

1. A process for producing olefins comprising:
   dehydrogenating a first n-alkane in a first dehydrogenation reaction zone comprising at least two reactors to produce a first effluent comprising at least one of a first n-olefin or a first diolefin;
   dehydrogenating at least one of a first isoalkane or a second n-alkane in a second dehydrogenation reaction zone comprising at least two reactors to produce a second effluent comprising at least one of a first isoolefin, a second n-olefin, or a second diolefin;
   wherein each reactor in the process is operated in a cyclic operation with sequential steps including a dehydrogenation cycle, a purge cycle, a regeneration cycle, and an evacuation/reduction cycle, and
   wherein operation of the reactors in the dehydrogenation cycle is staggered such that, inclusive of reactors in both the first and second dehydrogenation reaction zones, no two reactors are in the purge cycle at the same time and no reactors are in the evacuation/reduction cycle at the same time;
   compressing the first effluent;
   compressing the second effluent;
   removing a purge stream by condensation in a compressor inter-stage cooler;
   feeding the first and second effluents to a common separation train to separate the first and second effluents into two or more fractions;
   wherein the first n-alkane is selected from the group consisting of propane and n-butane, and wherein at least one of a first isoalkane or a second n-alkane, different from the first n- alkane, is selected from the group consisting of isobutane and isopentane.

2. The process of claim 1, wherein the first n-alkane is propane, the at least one of the first n-olefin or the first diolefin is propylene, the at least one of the first isoalkane or the second n-alkane is isobutane, and the at least one of the first isoolefin, the second n-olefin, or the second diolefin is isobutene.

3. The process of claim 1, wherein the first n-alkane is propane, the at least one of the first n-olefin or the first diolefin is propylene, the at least one of the first isoalkane or the second n-alkane is n-butane, and the at least one of the first isoolefin, the second n-olefin, or the second diolefin is at least one of n-butene or butadiene.

4. The process of claim 1, wherein the first n-alkane is n-butane, the at least one of the first n-olefin or the first diolefin is at least one of n-butene or butadiene, the at least one of the first isoalkane or the second n-alkane is isobutane, and the at least one of the first isoolefin, the second n-olefin, or the second diolefin is isobutene.

5. The process of claim 1, wherein the at least one of the first isoalkane or the second n-alkane is n-butane and isobutane, the at least one of the first isoolefin, the second n-olefin, or the second diolefin is at least one of isobutene, n-butene, or butadiene, the first n-alkane is propane, and the at least one of the first n-olefin or the first diolefin is propylene.

6. The process of claim 1, further comprising:
   dehydrogenating at least one of a second isoalkane or a third n-alkane in a third dehydrogenation reaction zone to produce a third effluent comprising at least one of a second isoolefin, a third n-olefin, or a third diolefin;
   compressing the third effluent; and
   feeding the third effluent to the common separation train;
   wherein the third n-alkane is selected from the group consisting of propane and n-butane, and the second isoalkane is selected from the group consisting of isobutane and isopentane.

7. The process of claim 6, wherein:
   the first n-alkane is propane, the at least one of the first n-olefin or the first diolefin is propylene, the at least one of the first isoalkane or the second n-alkane is at least one of n-butane and isobutane, the at least one of the first isoolefin, the second n-olefin, or the second diolefin is at least one of n-butene, isobutene, or butadiene, the at least one of the second isoalkane or the third n-alkane is isopentane, and the at least one of the second isoolefin, the third n-olefin, or the third diolefin is at least one of isopentane or isoprene.

8. The process of claim 6, wherein:
the first n-alkane is propane, the at least one of the first n-olefin or the first diolefin is propylene, the at least one of the first isoalkane or the second n-alkane is isobutane, the at least one of the first isoolefin, the second n-olefin, or the second diolefin is isobutene, the at least one of the second isoalkane or the third n-alkane is n-butane, and the at least one of the second isoolefin, the third n-olefin, or the third diolefin is at least one of n-butene or butadiene.

9. The process of claim 6, further comprising:
dehydrogenating a third isoalkane in a fourth dehydrogenation reaction zone to produce a fourth effluent comprising at least one of a third isoolefin or a fourth diolefin;
compressing the fourth effluent; and
feeding the fourth effluent to the common separation train;
wherein the third isoalkane is selected from the group consisting of isobutane and isopentane.

10. The process of claim 9, wherein:
the first n-alkane is propane, the at least one of a first n-olefin or a first diolefin is propylene,
the at least one of a first isoalkane or a second n-alkane is u-butane, and the at least one of a first isoolefin, a second n-olefin, or a second diolefin is at least one of n-butene or butadiene;
the at least one of a second isoalkane or a third n-alkane is isobutane, and the at least one of a second isoolefin, a third n-olefin, or a third diolefin is isobutene;
the third isoalkane is isopentane, and the at least one of a third isoolefin or a fourth diolefin is at least one of isopentene or isoprene.

11. The process of claim 1, further comprising:
combining an effluent comprising steam and hydrocarbons from the reactor in a purge cycle with the second effluent;
separating the steam from the hydrocarbons in the purge effluent and the second effluent.

12. The process of claim 11, wherein the separating the steam comprises condensing the steam in a compressor inter-stage cooler.

13. The process of claim 11, further comprising sequentially operating two or more valves disposed in a parallel flow arrangement for providing air, steam, and inerts, as required, from a common regeneration system to the reactors in the regeneration cycle and the reactor in the purge/evacuation/reduction cycle, and for providing propane, n-butane, isobutane, or isopentane, as required, to the reactors in the dehydrogenation cycle.

14. The process of claim 1, wherein each of the first and second dehydrogenation reaction zones comprise four reactors, the process further comprising:
operating two reactors in each of the reaction zones in a dehydrogenation cycle;
operating one reactor in each of the reaction zones in a regeneration cycle; and
operating one reactor in each of the reaction zones in a purge or evacuation/reduction cycle.

15. The process of claim 14, wherein operation of the reactors in the dehydrogenation cycle is staggered, such that the purge cycle, regeneration cycle, or evacuation/reduction cycle of the reactors in each of the reaction zones do not overlap.

16. The process of claim 1, wherein each of the first and second dehydrogenation reaction zones comprise five reactors, the process further comprising:
operating two reactors in each of the reaction zones in a dehydrogenation cycle;
operating two reactors in each of the reaction zones in a regeneration cycle; and
operating one reactor in each of the reaction zones in a purge or evacuation/reduction cycle.

17. The process of claim 1, further comprising recycling at least one of the two or more fractions to at least one of the first or second dehydrogenation reaction zones.

18. The process of claim 1, wherein the two or more fractions include a fraction comprising isobutene and isobutane, the process further comprising:
etherifying at least a portion of the isobutene; and
separating ethers from the isobutane.

19. The process of claim 1, further comprising recovering heat from at least one of the first effluent and the second effluent.

20. A process for producing olefins comprising:
dehydrogenating propane in a first dehydrogenation reaction zone comprising at least two reactors to produce a first effluent comprising propylene;
dehydrogenating isobutane in a second dehydrogenation reaction zone comprising at least two reactors to produce a second effluent comprising isobutene;
wherein each reactor in the process is operated in a cyclic operation with sequential steps including a dehydrogenation cycle, a purge cycle, a regeneration cycle, and an evacuation/reduction cycle, and
wherein operation of the reactors in the dehydrogenation cycle is staggered such that, inclusive of reactors in both the first and second dehydrogenation reaction zones, no two reactors are in the purge cycle at the same time and no reactors are in the evacuation/reduction cycle at the same time;
cooling the first effluent in an indirect heat exchanger to produce steam and a cooled first effluent;
cooling the second effluent in an indirect heat exchanger to produce steam and a cooled second effluent:
heating the propane fed to the first dehydrogenation reaction zone via indirect heat exchange with the cooled first effluent;
heating the isobutane fed to the second dehydrogenation reaction zone via indirect heat exchange with the cooled second effluent;
mixing and compressing the first and second effluents;
feeding the compressed effluents to a common separation train to recover an ethylene fraction, a propylene fraction, a propane fraction, at least one C4 fraction, and one or more fractions including heavy byproducts;
combining an effluent comprising steam and hydrocarbons from a reactor in a purge cycle with the second effluent;
separating the steam from the hydrocarbons in the purge effluent and the second effluent by condensing the steam in a compressor inter-stage cooler.

21. The process of claim 20, further comprising feeding n-butane to the second dehydrogenation reaction zone to produce the second effluent comprising isobutene and butadiene.

* * * * *